United States Patent [19]

Lamson et al.

[11] 4,233,467

[45] * Nov. 11, 1980

[54] DEHYDRATION OF α-METHYLBENZYL ALCOHOLS TO FORM MONOVINYLIDENE AROMATIC MONOMERS

[75] Inventors: Junior J. Lamson, Bay City; Richard H. Hall, Midland; Edward Stroiwas, Merrill; Larry D. Yats, Clare, all of Mich.

[73] Assignee: The Dow Chemical Company, Midland, Mich.

[*] Notice: The portion of the term of this patent subsequent to Sep. 20, 1994, has been disclaimed.

[21] Appl. No.: 19,945

[22] Filed: Mar. 12, 1979

Related U.S. Application Data

[63] Continuation-in-part of Ser. No. 817,937, Jul. 22, 1977, Pat. No. 4,150,059, which is a continuation-in-part of Ser. No. 601,946, Aug. 4, 1975, Pat. No. 4,049,736, which is a continuation-in-part of Ser. No. 39,889, May 22, 1970, abandoned.

[51] Int. Cl.² .................... C07C 15/00; C07C 15/10
[52] U.S. Cl. ................................ 585/437; 570/200
[58] Field of Search .................... 260/650 R; 585/437

[56] References Cited

U.S. PATENT DOCUMENTS

| | | | |
|---|---|---|---|
| 2,399,395 | 4/1946 | Shriver | 585/437 |
| 3,658,928 | 4/1972 | Skinner et al. | 585/437 |
| 4,049,736 | 9/1977 | Lamson et al. | 260/650 R |
| 4,150,059 | 4/1979 | Lamson et al. | 260/650 R |

FOREIGN PATENT DOCUMENTS

| | | | |
|---|---|---|---|
| 338262 | 11/1930 | United Kingdom | 585/437 |
| 589015 | 6/1947 | United Kingdom | 585/437 |

*Primary Examiner*—Brian E. Hearn

[57] ABSTRACT

α-Alkylbenzyl alcohol and substituted α-alkylbenzyl alcohols are converted in high yield and purity to styrene and substituted styrenes by contacting the alcohol in vapor phase with a high efficiency silica gel catalyst.

5 Claims, No Drawings

DEHYDRATION OF α-METHYLBENZYL ALCOHOLS TO FORM MONOVINYLIDENE AROMATIC MONOMERS

CROSS-REFERENCE TO RELATED APPLICATIONS

The present application is a continuation-in-part of our previous application Ser. No. 817,937, filed July 22, 1977, now U.S. Patent No. 4,150,059, which is a continuation-in-part of application Ser. No. 601,946, filed Aug. 4, 1975, now U.S. Pat. No. 4,049,736, which is a continuation-in-part of Application Ser. No. 39,889, filed May 22, 1970, abandoned.

BACKGROUND OF THE INVENTION

This invention relates to the vapor phase dehydration of α-alkylbenzyl alcohols and substituted analogues thereof to form styrene and substituted styrenes.

Dehydration of alcohols to their corresponding unsaturated structural compounds is well known in the art. Dehydration techniques are not now generally employed in the manufacture of styrene and many homologues thereof because standard dehydrogenation of ethylbenzene is considered to be a more economic route. In addition, styrenes produced by conventional dehydration techniques including those employing titania as the dehydration catalyst often contain enough ethylbenzene and other impurities to require extensive purification.

It is characteristic of standard dehydrogenation techniques employed in the production of styrene that fairly large quantities of unreacted ethylbenzene be present in the styrene fraction. Such quantities of ethylbenzene in the styrene fraction are substantial enough to cause loss of properties in polymers of such styrene fractions. Furthermore, due to the closeness of the boiling points of styrene and ethylbenzene, removal of ethylbenzene by distillation is expensive.

Conventional dehydration techniques for preparing styrene and substituted styrenes are not completely satisfactory in that substantial amounts of ethylbenzene and other difficult to separate impurities often remain or are produced. Such difficulties have been pointed out in prior publications such as U.S. Pat. Nos. 2,399,395 and 3,442,963.

Therefore, it would be highly desirable to provide a new, improved technique for producing styrene and substituted styrenes in high yield which contain little or no alkyl benzene impurities.

SUMMARY OF THE INVENTION

Accordingly, the present invention is an improved process for dehydrating α-alkylbenzyl alcohols and to form the corresponding styrene monomer in high yield and purity. This improved process comprises contacting an α-alkylbenzyl alcohol, as hereinafter described in detail, in vapor phase with a dehydration catalyst consisting essentially of silica gel having a surface area of at least 300 m²/g (hereinafter called high efficiency silica gel).

In the process of this invention, a highly efficient silica gel which has heretofore been employed as a support for other catalysts is used as the dehydration catalyst. Surprisingly, in the practice of this process, it is found that the employment of this high efficiency silica gel effectively increases the yield of the desired styrene and substantially reduces, and under optimum conditions, almost completely eliminates the formation of ethylbenzene and other impurities which are difficult to separate. In general, the desired monovinylidene aromatic monomer is produced in purity greater than about 99 mole percent and contains less than about 1, preferably less than about 0.5, mole percent of alkyl benzene impurity, so-called ethylbenzene impurity.

As a result, styrene monomers produced by this method require little or no further purification to remove impurities having lower boiling points nearly the same as the monomer; thus, expensive fractionation procedures are eliminated. Styrene polymers produced from these styrene monomers are found to have improved properties as a result of the increased purity.

DESCRIPTION OF THE PREFERRED EMBODIMENTS

For the purposes of this invention, the term "α-alkylbenzyl alcohol" includes α-alkylbenzyl alcohols, especially α-methylbenzyl alcohol and substituted analogues thereof. Such alcohols are represented by the general formula:

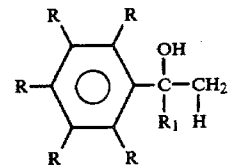

wherein R is hydrogen, alkyl having from 1 to 12 carbon atoms, e.g., methyl, t-butyl, t-amyl and other t-alkyl; halogen, e.g., bromo, chloro, and fluoro; or the like and $R_1$ is hydrogen or alkyl having from 1 to 4 carbon atoms.

Exemplary α-alkylbenzyl alcohols include α-methylbenzyl alcohol, ar-chloro-α-methylbenzyl alcohol, ar-bromo-α-methylbenzyl alcohol, ar-fluoro-α-methylbenzyl alcohol, ar-dichloro-α-methylbenzyl alcohol, ar-dibromo-ar-chloro-α-methylbenzyl alcohol, ar-chloro-α-ethylbenzyl alcohol, 4-chloro-2,5-difluoro-α-methylbenzyl alcohol, ar-(t-butyl)-α-methylbenzyl alcohol, ar-(t-amyl)-α-methylbenzyl alcohol, ar,α-dimethylbenzyl alcohol, α-ethyl-2-isopropyl-5-methylbenzyl alcohol, α-isobutyl-2,4,5-trimethylbenzyl alcohol, and the like. The preferred α-alkyl benzyl alcohol is α-methylbenzyl alcohol.

The above alcohols are known compounds and can be prepared by syntheses obvious to those skilled in the art. Illustratively, ar-alkyl-α-methylbenzyl alcohols can be prepared by the stepwise synthesis of (1) alkylating ethylbenzene with olefin in the presence of sulfuric acid in accordance with the method of Ipatieff et al., JACS, Vol. 58, 919 (1936), (2) oxidizing the alkylated ethylbenzene to the corresponding acetophenone-alcohol mixture as described by H. J. Sanders et al., I & E Chem., Vol. 45, 2 (1953), and (3) reducing the mixture by catalytic hydrogenation to the desired alcohol.

The silica gel employed in this invention is a silica gel particulate having a surface area of at least 300 m²/g thereby permitting intimate contact between the silica gel and alcohol vapor during the dehydration. It is desirable that the silica gel be in the form of a divided solid, preferably in the form of particles having a particle diameter less than 10 millimeters. Further the silica gel should be of a type that is not degraded or destroyed when contacted with large quantities of liquid or vaporous alcohol or water. Although good results are obtained with a number of grades of particulate silica gel, better results are obtained with the silica gel in the form of a particulate solid having particle diameters from about 20 to about 5000 micrometers and a surface area of at least about 300 square meters per gram, preferably from 300 to 900 m²/g. Of especial preference are the silica gels that are finely divided porous particles having an average pore diameter ranging from about 2 to about 200 Angstrom units and an average pore volume of at least 0.4 cc/g, preferably from about 0.60 to about 1.65 cc/g. Methods for preparing silica gel are well known to skilled artisans.

While products of highest purity are achieved by contacting the α-alkylbenzyl alcohol in vapor phase with the silica gel in the presence of from about 0.03 to about 25 parts by weight of water per part by weight of alcohol, preferably from about 0.5 to about 20 weight parts, especially from about 1 to about 2 parts of water per weight part of alcohol, styrenes of acceptable purity can be obtained without the addition of water. The omission of water from the alcohol reactant is particularly advantageous in large commercial scale dehydration processes for preparing styrene wherein small amounts, i.e., from 0.2 to 0.5 mole percent of ethylbenzene impurity can be tolerated. The practice of such process is easily accomplished by passing liquid or vaporous forms of the alcohol or mixtures of the alcohol and solvent over or through a bed or column of an effective heat transfer material such as silicon carbide, fused ceramic packing or noncorrosive metal packing. In such embodiments, a column having a lower portion of a bed of silica gel and an upper portion of the heat transfer agent can be made and the alcohol containing water is then passed downward into the column through the heat transfer agent and then through the silica gel bed. It is often desired to employ an organic carrier liquid which is a solvent for the alcohol but which can be easily removed by simple distillation. In such embodiments, the alcohol and carrier liquid are mixed together prior to vaporization of the alcohol mixture. Examples of suitable solvents include aromatic hydrocarbons such as toluene, benzene, xylene and the like as well as aromatic ketone precursors of the alcohols such as acetophenone.

Generally, the desirable temperatures of operation of the process of this invention are in the range of about 200° C. to 310° C., preferably from about 260° C. to about 320° C., especially from about 260° C. to about 290° C. In the dehydration of the higher boiling α-methylbenzyl alcohols, it is generally desirable to employ higher temperatures within the aforementioned ranges in order to insure contact between the silica gel and the alcohol in the vapor state. It is generally desirable to carry out dehydration at atmospheric pressure, although it is possible to achieve dehydration with relatively good purity and yield at subatmospheric to superatmospheric pressure, e.g., from about 0.2 to about 5 atmospheres. Vaporization of the alcohol, however, may be advantageously achieved by using reduced pressure. Vaporization may also be achieved by contacting the alcohol with steam or superheated steam substantially prior to dehydration.

The quantity of silica gel which effectively dehydrates the alcohol depends in part upon the rate at which the vaporous alcohol is to be passed through the silica gel bed or column, upon the surface area of the gel per unit of weight, upon the amount of water to be employed. Generally higher vapor flow rates and larger quantities of water require more silica gel to achieve effective dehydration.

Practice of the present invention as described hereinbefore yields the desired monovinylidene aromatic monomer, particularly styrene, in purity greater than 99 mole percent based on total product after simple distillation which separates the lower boiling styrene fraction from unreacted ketones and alcohols which boil at temperatures 60° F. more than styrene. The recovered styrene fraction contains less than one mole percent of ethylbenzene, preferably below about 0.5 mole percent.

The invention is further illustrated by the following examples which should not be construed as limiting the scope of the invention. All parts and percentages are by weight unless otherwise indicated.

EXAMPLE 1

A first mixture to 50 parts of α-methylbenzyl alcohol and 50 parts of toluene is preheated to 300° C. and mixed with 100 parts of steam at 300° C. The resulting steam/alcohol mixture is passed downward at a rate equivalent to that employed in Example 3 through a glass column (1" outside diameter×27" length) equipped with an electric furnace and containing a 14-inch upper layer of silicon carbide (8 mesh) preheated to 350° C. and a 6-inch lower layer (20 g) of silica gel (on 10 mesh, 300 m² of surface area/g, pore volume of 1 cc/g and sold as a catalyst support under the trade name Davison Silica Gel Grade 57 by Davison Chemical). Water and dehydrated organic product are condensed in the lower part of the column, collected and separated. The organic product is dried and distilled. The distilled product is determined by infrared spectroscopy and vapor phase chromatography to be 99+ mole percent styrene containing less than 0.5 mole percent of ethylbenzene. Overall conversion on the basis of starting alcohol is greater than 95 percent.

EXAMPLE 2

Following generally the procedure of Example 1 except (1) that no solvent (toluene) is employed, (2) the reactor is a stainless steel pipe (inside diameter of 1", length of 17" and wall thickness of 3/16") and (3) the temperature and quantity of added water are varied as indicated in Table I, several runs are carried out by passing a reactant alcohol feed containing α-methylbenzyl alcohol and varying amounts of steam through a heated tubular reactor packed with silica gel used in Example 1 and equipped for continuous feed of the alcohol feed containing steam. The results are reported in Table I.

TABLE I

| Run No. | Reactor Temp. °C. | Water/Alcohol Parts/Part | Residence Time(1) Sec. | % Conversion (2) | Ethyl Benzene Mole % |
|---|---|---|---|---|---|
| 1 | 265 | 3.3 | 2.7 | 95.3 | 0.053 |
| 2 | 289 | 1.6 | 2.8 | 98.9 | 0.060 |
| 3 | 287 | 0.6 | 3.7 | 98.6 | 0.105 |
| 4 | 273 | 0.0 | 12.0 | 97.5 | 0.194 |

(1)Average time in seconds that alcohol spends in tubular reactor.
(2)Mole percent of alcohol converted to styrene.
(3)Mole percent of ethylbenzene based on moles of styrene obtained.

As evidenced by the data of Table I, lower amounts of ethylbenzene impurities are obtained when employing the specified amounts of water than obtainable in the absence of water. However, as the results of Run No. 4 indicate, fairly low levels of ethylbenzene impurity are achieved by using the high efficiency silica gel in the absence of added water.

EXAMPLE 3

A mixture of 50 parts of 4-(t-butyl)-α-methylbenzyl alcohol and 50 parts of toluene is prepared. A reaction column (1″ outside diameter ×27″ length) is filled to a bed height of 8–9 inches with silica gel (8–10 mesh, 340 m² of surface area/g, 140 Å average pore diameter and sold as a catalyst support under the trade name Davison Silica Gel Grade 70 by Davison Chemical) and sufficient amount of silicon carbide (6 mesh) is added to the tube to increase total bed height to 16 inches. The reaction column is heated to 300° C. Water preheated to 300° C. and the mixture are added simultaneously into the feed end of the column at rates of 90 ml/hr and 45 ml/hr, respectively. An intimate admixture of steam and the alcohol mixture in vapor phase is formed and passes downward through the silicon carbide preheated to 350° C. which acts as a preheat section for the vapor and then through the silica gel to effect dehydration. Following passage through the silica gel, water and organic product are condensed in the column, and collected. The dehydrated organic product is decanted, dried and distilled. The distilled product is determined by infrared spectroscopy and vapor phase chromatography to be 4-(t-butyl)styrene at 99 percent or greater purity. Overall conversion on basis of amount of starting alcohol is greater than 90 percent.

Polymerization of the 4-(t-butyl)styrene by heating in the presence of benzoyl peroxide yields a polymer which is soluble in toluene at 20° C.

EXAMPLE 4

Several sample runs are carried out generally according to the procedure of Example 3. In these runs, mixtures of 50 parts of 4-(t-butyl)-α-methylbenzyl alcohol and 50 parts of toluene are prepared and mixed with varying amounts of steam. The vaporous steam/alcohol mixture is passed downward into a glass column (1″ OD ×27″ length) having a 14″ upper bed of silicon carbide (10 mesh) preheated to varying temperatures and a 6″ lower bed of silica gel (same as in Example 3). Water and dehydrated organic product are condensed, collected and separated as in Example 3. The results are recorded in Table II.

To show the particular advantage of employing added water in this system, Run No. 11 is made under conditions similar to the above runs with the exception that no water is added to the alcohol at any point prior to or during dehydration. The results of this control run are also recorded in Table II. To indicate upper limits as to temperature during dehydration, two control runs (Run Nos. $C_1$ and $C_2$) employing varying amounts of water are also carried out in accordance with the procedures employed in the above sample runs. The results are recorded in Table II.

TABLE II

| Sample Run No. | Water/- Alcohol pts per pt | Reaction Temp.[1] °C. | Impurities[2] Isopropenyl Styrene, Mole % | 4-(t-Butyl)Ethyl- benzene, Mole % | Polymer[3] Solubility |
|---|---|---|---|---|---|
| 1 | ~5.0 | 410 | 0 | 0.15 | Soluble |
| 2 | ~1.4 | 406 | 0 | 0.15 | Soluble |
| 3 | ~0.84 | 406 | 0 | 0.14 | Soluble |
| 4 | ~0.56 | 395 | 0 | 0.13 | Soluble |
| 5 | ~20.0 | 393 | 0 | 0.2 | Soluble |
| 6 | ~20.0 | 445 | 0 | 0.2 | Soluble |
| 7 | ~20.0 | 505 | <0.02 | 0.7 | Soluble |
| 8 | ~0.50 | 400 | 0 | 0.1 | Soluble |
| 9 | ~0.50 | 448 | 0 | 0.4 | Soluble |
| 10 | ~0.50 | 506 | <0.02 | 0.6 | Soluble |
| 11 | ~0 | 400 | 0.12 | 0.23 | Insoluble |
| $C_1$* | ~20.0 | 550 | >0.11 | 1.4 | Insoluble |
| $C_2$* | ~0.50 | 550 | >0.18 | 1.5 | Insoluble |

*Not an example of the invention
[1]Reaction temperature corresponds to temperature of silicon carbide heat transfer means.
[2]Approximate mole % of the specified impurity based on moles of p-(t-butyl)-styrene produced. Determined by gas phase chromatography and infrared spectroscopy.
[3]Solubility of 10% p-(t-butyl)styrene polymer in toluene at 23° C.

EXAMPLE 5

Several sample runs are carried out essentially according to Example 3 except that a wide range of temperatures are employed. In the several runs, mixtures of 50 parts of ar-(t-butyl)-α-methylbenzyl alcohol containing ~7 mole percent of ar-(t-butyl)acetophenone and 50 parts of toluene are prepared. A glass column (1″ OD and 16″ length) equipped with an electric furnace is filled to a height of 3.5″ with silicon carbide (8 mesh, 42 grams), to a total height of 13.5″ with silica gel (same as in Example 3, 50 grams), and to a total height of 16.0″ with silicon carbide (8 mesh, 40 grams) and preheated to varying temperatures from 200° to 500° C. for the several runs. Steam superheated to at least 550° C. and the alcohol/toluene mixture are added simultaneously into the feed end of the column at rates of 100 ml/hour (measured as condensed water) and 50 ml/hour, respectively. An intimate admixture of steam and the alcohol mixture in vapor phase is formed and passed downward through the heat transfer agent and the silica gel to effect dehydration. The water and organic product are then condensed, collected and separated. The organic product is distilled and dried, and its constituency is determined by infrared spectroscopy and vapor phase chromatography. The results are shown in Table III.

To point out the advantage of silica gel catalysts over conventional dehydration catalysts, several control runs ($C_4$–$C_8$) are made employing essentially the same procedure used above except that a titania dehydration catalyst (4–8 mesh, and 70 m² of surface area/g) is substituted for silica gel. The dehydration column has a 3.5″ bottom layer of silicon carbide (8 mesh), a 10″ middle layer of titania catalyst and a 2.5″ top layer of silicon carbide. The organic product is recovered and analyzed by infrared spectroscopy and vapor phase chromatography and the results are recorded in Table III.

ency is determined by the means described above. The results are also recorded in Table IV.

TABLE IV

| Sample Run No. | Catalyst | p-(t-butyl)-styrene | m-(butyl)-styrene | ar-(t-butyl) ethylbenzene | ar-(t-butyl)toluene and ar-(t-butyl)benzene | ar-(t-butyl)acetophenone ar-(t-butyl)-α-methyl-benzyl alcohol, ppm |
|---|---|---|---|---|---|---|
| 1 | Silica Gel | 96.09 | 3.77 | 0.10 | 0.04 | <25 |
| C9* | Alumina | 96.52 | 2.32 | 1.08 | 0.08 | ~45 |

*Not an example of the invention

TABLE III

| Sample Run No. | Reaction Temp, °C. | Catalyst | ar-(t-butyl)-Styrene | ar-(t-butyl)-ethylbenzene | ar-(t-butyl)-Acetophenone | ar-(t-butyl)-α-methylbenzyl Alcohol |
|---|---|---|---|---|---|---|
| 1 | 50 | Silica gel | 92.1 | 0.5 | 4.4 | 3.0 |
| 2 | 30 | Silica gel | 95.3 | 0.3 | 4.5 | — |
| 3 | 50 | Silica gel | 95.9 | 0.3 | 3.9 | — |
| 4 | 40 | Silica gel | 97.2 | 0.2 | 2.6 | — |
| 5 | 50 | Silica gel | 95.3 | 0.2 | 4.5 | — |
| 6 | 30 | Silica gel | 94.2 | 0.5 | 5.3 | — |
| C4* | 50 | Anhydrous titania | 97.3 | 0.4 | 2.3 | — |
| C5* | 30 | Anhydrous titania | 97.2 | 0.6 | 2.2 | — |
| C6* | 50 | Anhydrous titania | 94.1 | .9 | 4.0 | — |
| C7* | 40 | Anhydrous titania | 91.9 | 1.4 | 2.7 | — |
| C8* | 50 | Anhydrous titania | 83.5 | 2.3 | 3.3 | — |

*Not an example of the invention.

As evidenced by Table III, significantly larger quantities of ar-(t-butyl)ethylbenzene are generally produced in dehydrations employing titania as catalyst than those employing silica gel under essentially the same conditions. The ar-(t-butyl)ethylbenzene is difficult to separate from ar-(t-butyl)-styrene whereas ar-(t-butyl)acetophenone is separated from either of the above by simple distillation.

EXAMPLE 6

A solution of 50 parts of ar-(t-butyl)-α-methylbenzyl alcohol containing ~7 mole percent of ar-(t-butyl)acetophenone in 50 parts of toluene is mixed with superheated steam (550° C.) in a ratio of 2 parts of water to one part of the mixture. The steam/alcohol mixture is passed downward through a glass column (1″ OD×21″ length) containing a 10″ upper layer of silicon carbide and a 10″ lower layer of silica gel (same as in Example 3). The temperature at the top of the column is 350° C. and at the bottom of the column is 325° C. The water and organic product is distilled and dried, and its constituency is determined by infrared spectroscopy and vapor phase chromatography. The results are shown in Table IV.

For the purposes of comparison, a control run (C9) is carried out by following the above process except that alumina (4–8 mesh and 210 m²/g of surface area/gram) is substituted for silica gel as dehydration catalyst. The organic product is distilled and dried and its constitu-

EXAMPLE 7

The dehydration process of the present invention is carried out in a continuous manner by continuously feeding molten ar-(t-butyl)-α-methylbenzyl alcohol at 200 lb/hr and water superheated to 550° C. at 400 lb/hr into a column (18″ OD×6′8″ length). The column contains a 3′4″ upper bed of metallic heat transfer material preheated to 350° C. and a 3′4″ lower bed of silica gel (same as in Example 3). The temperature at the lower end of the column is 325° C. The dehydrated organic product is continuously collected at the lower end of the column and then recovered at 99+ percent purity by simple distillation. The dehydrated product is determined by infrared spectroscopy to be ar-(t-butyl)-styrene.

EXAMPLE 8

Several samples of ar-chloro-α-methylbenzyl alcohol containing small amounts of ar-chloro-acetophenone are continuously dehydrated by mixing the liquid alcohol with varying amounts of superheated steam (550° C.) and passed as vapor phase through the column described in Example 4. Dehydration temperatures for the various runs are also varied. The amounts of low boiling components are shown in Table V.

For the purposes of comparison, similar samples of ar-chloro-α-methylstyrene also containing small amounts of ar-chloro-acetophenone are continuously dehydrated in the same manner except that no water is added during the process. The amounts of low boiling components for these runs (Sample Run Nos. 5, 6 and 7) are also shown in Table V.

TABLE V

| Sample Run No. | Water/Alcohol, ml/100 ml | Reaction Temp, °C. | Low Boiling Components of Reaction Mixture, parts(1) | | | Low Boiling Impurities/ar-chlorostyrene pts/100 pts |
|---|---|---|---|---|---|---|
| | | | ar-chloro-styrene | ar-chloro-ethylbenzene | Other | |
| 1 | 3 | 400 | 62.89 | 1.10 | 0.22 | ~2.1 |
| 2 | 5 | 400 | 76.19 | 0.88 | 0.19 | ~1.4 |
| 3 | 25 | 350 | 73.91 | 0.16 | 0.09 | ~0.34 |
| 4 | 50 | 400 | 78.11 | 0.03 | ND** | ~0.04 |
| 5 | 0 | 400 | 55.80 | 1.88 | 0.45 | ~4.2 |
| 6 | 0 | 350 | 58.90 | 0.89 | 0.27 | ~1.80 |
| 7 | 0 | 400 | 63.64 | 1.61 | 0.45 | ~3.23 |

**None detected
(1)Higher boiling components including chloroacetophenone and ar-chloro-α-methylbenzyl alcohol comprise the remaining reaction mixture having a total of 100 parts.

EXAMPLES 9–14

In accordance with the continuous dehydration process of Example 4, several substituted α-methylbenzyl alcohols are dehydrated to the corresponding substituted styrenes thereof. The results obtained are comparable to those obtained in Example 4. The alcohols successfully dehydrated are as follows:

ar-t-butyl-α,α-dimethylbenzyl alcohol
ar-dichloro-α-methylbenzyl alcohol
ar-dibromo-α-methylbenzyl alcohol
ar-di-t-butyl-α-methylbenzyl alcohol
ar-(1-ethyl-1-methylpentyl)-α-methylbenzyl alcohol
ar-t-butyl-ar-methyl-α-methylbenzyl alcohol.

Several dehydration runs are also carried out using silica gel catalysts having different mesh sizes in the range from about 2 to about 400 and surface areas in the range from about 300 to about 900 m$^2$/g with good results.

What is claimed is:

1. A process for preparing a monovinylidene aromatic monomer by dehydrating α-methylbenzyl alcohol which comprises a dehydration step of contacting the alcohol in vapor phase with a dehydration catalyst consisting essentially of silica gel in the form of a divided solid having a surface area of at least about 300 m$^2$/g, said dehydration step being carried out at temperatures from about 200° to about 510° C., and a step of subjecting the product of the dehydration step to simple distillation to obtain styrene in purity greater than 99 mole percent which styrene contains less than 1 mole percent of ethylbenzene impurity.

2. The process according to claim 1 wherein the temperature is in the range from about 260° to about 320° C.

3. The process according to claim 2 wherein the silica gel is a divided, porous solid having an average pore diameter ranging from about 2 to about 200 Angstrom units.

4. The process of claim 1 wherein the temperature is in the range from about 260° to about 290° C.

5. The process of claim 1 wherein the silica gel is a divided, porous solid having an average pore diameter ranging from about 2 to about 200 Angstrom units.

* * * * *